United States Patent
Skogvall

(10) Patent No.: US 9,943,542 B2
(45) Date of Patent: Apr. 17, 2018

(54) COMPOSITIONS AND METHODS FOR OBTAINING AN IMPROVED LUNG FUNCTION

(71) Applicant: PHARMALUNDENSIS AB, Lund (SE)

(72) Inventor: Staffan Skogvall, Lund (SE)

(73) Assignee: PHARMALUNDENSIS AB, Lund (SE)

( * ) Notice: Subject to any disclaimer, the term of this patent is extended or adjusted under 35 U.S.C. 154(b) by 24 days.

(21) Appl. No.: 15/036,953

(22) PCT Filed: Nov. 20, 2014

(86) PCT No.: PCT/EP2014/075098
§ 371 (c)(1),
(2) Date: May 16, 2016

(87) PCT Pub. No.: WO2015/075111
PCT Pub. Date: May 28, 2015

(65) Prior Publication Data
US 2016/0271170 A1    Sep. 22, 2016

(30) Foreign Application Priority Data

Nov. 20, 2013    (SE) ...................................... 1351373

(51) Int. Cl.
| | |
|---|---|
| *A61K 33/20* | (2006.01) |
| *A61K 33/18* | (2006.01) |
| *A61K 9/00* | (2006.01) |
| *A61K 9/50* | (2006.01) |
| *A61K 45/06* | (2006.01) |
| *A61K 33/00* | (2006.01) |
| *A61K 33/44* | (2006.01) |

(52) U.S. Cl.
CPC ............ *A61K 33/20* (2013.01); *A61K 9/0053* (2013.01); *A61K 9/501* (2013.01); *A61K 33/00* (2013.01); *A61K 33/18* (2013.01); *A61K 33/44* (2013.01); *A61K 45/06* (2013.01)

(58) Field of Classification Search
CPC ...... A61K 45/06; A61K 9/501; A61K 9/0053; A61K 33/44; A61K 33/18; A61K 33/00
See application file for complete search history.

(56) References Cited

U.S. PATENT DOCUMENTS 6,024,882 A * 2/2000 McNeilly ................ C02F 1/283
                                                                  210/192
2010/0266573 A1    10/2010    Skogvall
2010/0272814 A1    10/2010    Skogvall

FOREIGN PATENT DOCUMENTS

EP    2222314 A1    9/2010

OTHER PUBLICATIONS

Wolff, "Perchlorate and the Thyroid Gland", Pharmacological Reviews, 1998, vol. 50, No. 1, p. 89-105.*
Lamm et al., "Perchlorate dosage on thyroid—laboratory confirmation of occupational epidemiology finding", Annals of Epidemiology, vol. 12, Issue 7, Oct. 2002, pp. 510-511.*
Greer, et al, "Health effect assessment for environmental perchlorate contamination: The dose response for inhibition of thyroidal radioiodide uptake in humans". Environmental Health Perspectives 110 (9): 927-937, 2002.
Wolff, "Perchlorate and the Thyroid Gland," Pharmacological Reviews 1998 50 (1): 89-105.
Lecat-Guillet, et al., "Small-Molecule Inhibitors of Sodium Iodide Symporter Function," Chem. Bio. Chem. 2008, 9, pp. 889-895.
Lidenthal, et al., "Characterization of small-molecule inhibitors of the sodium iodide symporter," Journal of Endocrinology (2009) 200, pp. 357-365.
Nicola, et al., "The Na+/I- symporter mediates active iodide uptake in the intestine," Am J Physiol Cell Physiol. Apr. 2009 vol. 296(4) pp. C654-C662.
Rubin BK. et.al. "Iodinated glycerol has no effect on pulmonary function, symptom score, or sputum properties in patients with stable chronic bronchitis." Chest. Feb. 1996; 109(2): 348-352.
Tonacchera, et al., "Relative Potencies and Additivity of Perchlorate, Thiocyanate, Nitrate, and Iodide on the Inhibition of Radioactive Iodide Uptake by the Human Sodium Iodide Symporter," Thyroid, vol. 14, No. 12, 2004 (8 pages).
International Search Report dated Jan. 30, 2015 for international application PCT/EP2014/075098, filed on Nov. 20, 2014 and published as WO 2015/075111 on May 28, 2015 (Applicant—Pharmalundensis AB // Inventor—Skogvall) (4 pages).
Written Opinion dated Jan. 30, 2015 for international application PCT/EP2014/075098, filed on Nov. 20, 2014 and published as WO 2015/075111 on May 28, 2015 (Applicant—Pharmalundensis AB // Inventor—Skogvall) (4 pages).
International Preliminary Report on Patentability dated Jan. 29, 2016 for international application PCT/EP2014/075098, filed on Nov. 20, 2014 and published as WO 2015/075111 on May 28, 2015 (Applicant—Pharmalundensis AB // Inventor—Skogvall) (18 pages).
Chang, et al., "Differentiating COPD from Asthma in Clinical Practice," Journal of Intensive Care Medicine, 2007, vol. 22, 300-309.
Rogers, "Mucoactive drugs for asthma and COPD: any place in therapy?" Expert Opin. Investig. Drugs. Jan. 2002;11(1):15-35.

* cited by examiner

*Primary Examiner* — Jianfeng Song
(74) *Attorney, Agent, or Firm* — Ballard Spahr LLP

(57) ABSTRACT

A pharmaceutical composition for obtaining an improved lung function in a human or an animal lung affected by airway obstruction such as COPD or asthma, is provided. The composition comprises a pharmacologically effective amount of activated carbon comprising adsorbed iodine and/or an adsorbed iodide salt and a sodium/iodide symporter inhibitor, such as perchlorate. Additionally, a method for obtaining an improved lung function in a human or animal lung affected by airway obstruction, such as COPD or asthma, is provided. The method comprises the steps of administering a pharmacologically effective amount of activated carbon comprising adsorbed iodine and/or an adsorbed iodide salt, and administering a sodium/iodide symporter inhibitor, such as perchlorate, in connection to the administration of the pharmacologically effective amount of activated carbon comprising adsorbed iodine and/or an adsorbed iodide salt.

4 Claims, No Drawings

COMPOSITIONS AND METHODS FOR OBTAINING AN IMPROVED LUNG FUNCTION

CROSS-REFERENCE TO RELATED APPLICATIONS

This Application is a U.S. National Phase Application of International Application No. PCT/EP2014/075098, filed Nov. 20, 2014, which claims the benefit of Swedish Application No. 1351373-4, filed Nov. 20, 2013, which are both incorporated herein by reference in their entirety.

FIELD OF THE INVENTION

The present invention pertains to a pharmaceutical composition for obtaining an improved lung function in a human or an animal lung affected by airway obstruction. Additionally, the present invention pertains to pharmaceutical compositions for use in treatment of chronic obstructive pulmonary disease and/or asthma, and methods for obtaining an improved lung function in a human or animal lung affected by airway obstruction.

BACKGROUND OF THE INVENTION

Chronic obstructive pulmonary disease (COPD), which is also known as chronic obstructive lung disease (COLD), chronic obstructive airway disease (COAD), chronic airflow limitation (CAL), and chronic obstructive respiratory disease (CORD), is a lung disease which primary symptoms include persistent obstruction in the airways, shortness of breath, cough, and sputum production.

COPD is often associated with tobacco smoking and is characterized by inflammation in the airways and a gradual decline in lung function. As the disease progresses during many years, the airway obstruction can become very severe, leading to extreme dyspnea during both exercise and rest and, eventually, lung failure. At this stage, lung function examinations with spirometry usually reveal a loss of lung capacity by 50% or more. Other severe symptoms often appear at this time as well, such as weight loss, depression and cardiac disease. The mortality risk is high in these patients. The established pharmaceutical treatments for these patients are anti-cholinergics, beta2-agonists and steroids, which however normally only give minor improvements. Causing over 3 million deaths in 2011, COPD is ranked as the fourth leading cause of death worldwide (World Health Organization. "The top 10 causes of death". Fact sheet No 310. July 2013). Due to the aging population mortality is expected to increase in many countries. The economic burden of COPD in the U.S. was estimated at $42.6 billion in health care costs and lost productivity during 2007. Thus, there is urgent need for new and effective treatments for COPD.

Asthma is characterized by chronic inflammation of the airways with mainly reversible airway obstruction and bronchial hyper-reactivity. Asthma is thought to be the result of a combination of genetic and environmental factors. Asthma is usually treatable with steroids and bronchodilators, however, 10% of asthmatics have severe symptoms in spite of maximum treatment. There is also an overlap between COPD and asthma, often rendering a firm diagnosis difficult to obtain (Chang, J.; Mosenifar, Z. "Differentiating COPD from Asthma in Clinical Practice". Journal of Intensive Care Medicine, 2007, vol. 22, 300-309]).

There have also been reports about obstructive pulmonary diseases, mainly asthma, in animals such as cats and dogs. As in humans, these animals get an obstruction of the airways when the bronchi fill up with mucous and go into spasms (bronchoconstriction). It is far more common in cats than dogs, and particularly in Siamese and Himalayan cat breeds (AnimalHospitals-USA, 2007).

Iodides have been used for many years as expectorants, for instance potassium iodide. However, clinical efficacy of these substances has not been conclusively demonstrated and they may induce thyroid disease (Rogers D F. "Mucoactive drugs for asthma and COPD: any place in therapy?" Expert Opin. Investig. Drugs. 2002 January; 11(1):15-35). Iodinated glycerol has been suggested as a potentially less toxic product, but clinical trials have shown it to lack significant improvement in pulmonary function following 16 weeks treatment with iodinated glycerol. Long term use has also been connected with side effects such as iodine poisoning (Rubin B K. et. al. "Iodinated glycerol has no effect on pulmonary function, symptom score, or sputum properties in patients with stable chronic bronchitis." Chest. 1996 February; 109(2):348-52).

Iodine is a vital element found in two hormones in humans; thyroxine (T4) and triiodothyronine (T3). They stimulate the body including growth and development. Iodine is actively pumped into the thyroid cells by the sodium/iodide symporter (also called iodide pump or Na+– I– pump) and T4 and T3 regulate metabolism. Furthermore, it has recently been shown that the active uptake of iodide in the intestine is caused by this pump. "Am J Physiol Cell Physiol. 2009 April; 296(4):C654-62. doi: 10.1152/ajpcell.00509.2008. The sodium/iodide symporter is also responsible for absorption of iodide in the kidney, which prevents loss of iodide in the urine.

Activated carbon is known for treating poisoning and as an adjunct to diet for occasional diarrhoea. Medical coal efficiently binds a large number of toxins and may thus prevent harmful substances such as pharmaceuticals, chemicals and bacterial toxins into the body. Activated charcoal has a very large surface area; 1 gram has a surface area of 300-2000 $m^2$ (GREENWOOD, N. N. et. al. "Chemistry of the Elements" Pergamon Press 1984). The term activated carbon also comprises what is meant by the term activated charcoal. Impregnated activated charcoals are carbonaceous adsorbents which have chemicals finely distributed on their internal surface. The impregnation optimizes the existing properties of the activated charcoal giving a synergism between the chemicals and the charcoal (Carbo Tech-Aktivkohlen GmbH. Franz-Ficher-Weg, vol. 61, D-45307, Germany).

It has been shown that iodinated activated charcoal (IAC) can improve lung function on patients with COPD (Skogvall). In EP 2 222 314 B1 is disclosed a method of treating COPD by using iodine on activated carbon. The iodinated activated carbon is administered orally, and it is shown that the carbon or iodine alone does not improve the lung function. Only when iodine was adsorbed on the activated charcoal was there an improved lung function.

Recently, a "Proof of concept" clinical study has confirmed the positive effects by IAC on the lung function of COPD patients, with a significant improvement of the pulmonary function ($FEV_1$ baseline, Forced Expiratory Volume in 1 second) in patients who received IAC, but not placebo. However, the improvement of lung function was only moderate (average 8.2% better than placebo after the 8 week treatment).

It was felt that it should be possible to improve the lung function even further, and it was therefore examined if additional substances could improve the lung function even more.

SUMMARY OF THE INVENTION

Accordingly, the present invention discloses that a combination of activated carbon comprising adsorbed iodine ($I_2$) and/or an adsorbed iodide salt and an inhibitor of the sodium/iodide symporter surprisingly causes a synergistic improvement of the lung function of individuals with pulmonary obstruction.

When IAC was taken together with the sodium/iodide symporter inhibitor potassium perchlorate, there was an almost doubling of the improvement of the lung function ($FEV_1$) compared to when IAC was taken alone. Also, the combination (IAC+perchlorate) reduced the patient's problems with cough and sputum more than when only IAC was given. This synergistic effect by adding perchlorate to IAC is very surprising, because perchlorate reduces the absorption of iodide from the intestine. If the effect by IAC somehow was that iodine has a direct positive effect on the airways, one would expect that a reduced absorption of iodide from the intestine would result in a reduced positive effect on the airways. Also, use of only perchlorate did not improve the lung function at all. Thus, the combination of IAC and perchlorate apparently results in a synergistic improvement of the lung function, compared to when IAC and perchlorate are taken as single treatment.

For these purposes a pharmaceutical composition for obtaining an improved lung function in a human or an animal lung affected by airway obstruction is provided, such as COPD or asthma, said composition comprising a pharmacologically effective amount of activated carbon comprising adsorbed iodine and/or an adsorbed iodide salt and a sodium/iodide symporter inhibitor.

Additionally, a method for obtaining an improved lung function in a human or animal lung affected by airway obstruction, such as COPD or asthma, is provided, said method comprising the steps of administering a pharmacologically effective amount of activated carbon comprising adsorbed iodine and/or an adsorbed iodide salt, and administering a sodium/iodide symporter inhibitor in connection to the administration of the pharmacologically effective amount of activated carbon comprising adsorbed iodine and/or an adsorbed iodide salt.

Further advantageous features of the invention are defined in the dependent claims. In addition, advantageous features of the invention are elaborated in embodiments disclosed herein.

DESCRIPTION OF PREFERRED EMBODIMENTS

A pharmacologically effective amount of activated carbon comprising adsorbed iodine and/or an adsorbed iodide salt in combination with a sodium/iodide symporter inhibitor for producing improvement of lung function is described.

It has previously been found that treatment of COPD patients for 8 weeks with IAC only resulted in a moderate increase of lung function (8.2% increase of $FEV_1$ baseline compared to placebo). However, it has now surprisingly been found that addition of a sodium/iodide symporter inhibitor (potassium perchlorate) gives a further synergistic improvement of the lung function.

Perchlorated is known to be a powerful sodium/iodide symporter inhibitor ($ClO_4^-$). Perchlorate functions as a competitive inhibitor of the sodium/iodide symporter (NIS) which controls the iodide uptake in the intestine, thyroid gland, and kidneys. Studies have shown that already low levels of above 0.007 milligrams per kilogram a day (mg/(kg·d)) perchlorate can temporarily inhibit the thyroid gland's ability to adsorb iodine from the bloodstream (Greer, M. A. et. al "Health effect assessment for environmental perchlorate contamination: The dose response for inhibition of thyroidal radioiodide uptake in humans". Environmental Health Perspectives 110 (9): 927-937, 2002). Perchlorate is neither metabolised nor stored in the body (J. Wolff. "Perchlorate and the Thyroid Gland". Pharmacological Reviews 1998 50 (1): 89-105.)

Thiocyanate ($SCN^-$) is also a sodium/iodide symporter inhibitor. While the relative potency of thiocyanate for inhibiting iodide uptake by the sodium/iodide symporter is lower than that of perchlorate on a molar concentration basis in serum, it offers an alternative sodium/iodide symporter inhibitor for an individual where perchlorate is unsuitable (Tonacchera M. et. al. "Relative potencies and additivity of perchlorate, thiocyanate, nitrate and iodide on the inhibition of radioactive iodide uptake by the human sodium/iodide symporter." Thyroid 2004: 14:1012-1019). Other possible sodium/iodide symporter inhibitors include nitrate ($NO_3^-$), perrhenate ($ReO_4^-$), hydrogen phosphate ($HPO_4^{2-}$), fluoride (F), sulfate ($SO_4^{2-}$), and pharmaceutically acceptable salts thereof, dysidenin, isodysidenin, HMA [5-(N,N-hexamethylene)amiloride], DMA [5-(N,N-dimethyl)amiloride], econazole, miconazole, ketoconazole and terconazole. A preferred sodium/iodide symporter inhibitor is perchlorate or nitrate.

The present invention discloses the use of a pharmacologically effective amount of activated carbon comprising iodine and/or an adsorbed iodide salt in combination with a sodium/iodide symporter inhibitor, such as perchlorate, in the manufacture of a medicament for producing an improved lung function in the lungs of a human or an animal with chronic obstructive pulmonary disease (COPD) or asthma.

It has been thought that iodide perhaps is responsible for the beneficial effect of IAC by directly influencing the airways in a human or an animal lung affected by airway obstruction. However, the discovery that the combination of IAC and perchlorate has a synergistic positive effect on lung function, in spite of perchlorate reducing the intestinal uptake of iodide, is contrary to the belief of the skilled person in the art.

Preferred administration forms for the pharmaceutical composition of the invention are pharmaceutical compositions for oral intake, such as tablets, tablets with disintegrants, capsules which disintegrate relatively fast in the stomach such as gelatin capsules and pullulan capsules, standard capsules (gelatine, vegetable or pullulan), wherein the tablets and capsules comprise activated carbon comprising adsorbed iodine and/or an adsorbed iodide salt and optionally comprise a sodium/iodide symporter inhibitor, such as perchlorate and any of flavor, colour, preservative, sweetener excipient.

Preferred iodine or iodide salt concentration is from 1% to 20% w/w of the activated charcoal, in particular from 3% to 17% w/w of the activated charcoal, most preferred from 5 to 13 w/w of the activated charcoal.

Daily doses to a human of iodine and/or iodide salt administered in form of the pharmaceutical composition are from 5 mg to 5,000 mg, in particular from 25 mg to 1,000 mg, most preferred from 50 mg to 500 mg.

Doses administered to a human of activated carbon comprising adsorbed iodine and/or an adsorbed iodide salt are from 0.10 g to 500 g daily, in particular from 0.5 g to 100 g daily, most preferred from 1 g to 25 g daily.

Daily doses to a human of sodium/iodide symporter inhibitor, such as perchlorate, administered in form of the pharmaceutical composition are from 1 mg to 1000 mg, in particular from 25 mg to 500 mg, most preferred from 50 mg to 250 mg.

The daily doses to a human of sodium/iodide symporter inhibitor, such as perchlorate, adsorbed iodine and/or iodide salt and activated carbon comprising adsorbed iodine and/or an adsorbed iodide salt, according to above, may be combined, such that perchlorate is administered in form of the pharmaceutical composition from 1 mg to 1000 mg, in particular from 25 mg to 500 mg, most preferred from 50 mg to 250 mg, while adsorbed iodine and/or iodide salt is administered from 5 mg to 5,000 mg, in particular from 25 mg to 1,000 mg, most preferred from 50 mg to 500 mg, and activated carbon comprising adsorbed iodine and/or an adsorbed iodide salt are from 0.10 g to 500 g daily, in particular from 0.5 g to 100 g daily, most preferred from 1 g to 25 g daily.

Perchlorate can be in the form of a perchlorate salt, such as sodium perchlorate and potassium perchlorate. Thiocyanate can be in the form of a thiocyanate salt, such as potassium thiocyanate and sodium thiocyanate. Nitrate can be in the form of a thiocyanate salt, such as potassium nitrate ($KNO_3$) and sodium nitrate ($NaNO_3$).

The adsorbed iodide salt may be selected from a group of alkali metal iodides and earth alkali iodides. Typical examples of such iodides that could be used in the present invention are NaI, KI, $MgI_2$, and $CaI_2$.

The ratio between the adsorbed iodine and/or iodide salt in the activated carbon comprising adsorbed iodine and/or iodide salt and the sodium/iodide symporter inhibitor may be selected to be in the interval from 200:1 to 1:5. When the sodium/iodide symporter inhibitor is perchlorate, thus the ratio between the adsorbed iodine and/or iodide salt in the activated carbon comprising adsorbed iodine and/or iodide salt and perchlorate may be selected to be in the interval from 200:1 to 1:5. The ratio between the adsorbed iodine and/or iodide salt in the activated carbon comprising adsorbed iodine and/or iodide salt and the sodium/iodide symporter inhibitor may even more preferably be selected to be in the interval from 100:1 to 1:1. When the sodium/iodide symporter inhibitor is perchlorate, thus the ratio between the adsorbed iodine and/or iodide salt in the activated carbon comprising adsorbed iodine and/or iodide salt and perchlorate may even more preferably be selected to be in the interval from 50:1 to 1:1.

The activated carbon comprising adsorbed iodine and/or an adsorbed iodide salt and sodium/iodide symporter inhibitor, such as perchlorate, may be administered to the intestine of a human or an animal in need of an improved lung function, in a pharmaceutically acceptable form, in particular in form of a tablet or capsule comprising elemental iodine/iodide salt on activated charcoal.

The activated carbon comprising adsorbed iodine and/or an adsorbed iodide salt and a sodium/iodide symporter inhibitor may be administered to the intestine of a human or an animal in form of a tablet, wherein the tablet comprises disintegrant for fast release of the tablet contents in the stomach.

The activated carbon comprising adsorbed iodine and/or an adsorbed iodide salt and sodium/iodide symporter inhibitor, such as perchlorate, may be administered to the intestine of a human or an animal in form of a capsule, wherein the capsule shell is comprised by gelatin or pullulan for fast release of the capsule contents, or a vegetable capsule.

The activated carbon comprising adsorbed iodine and/or an adsorbed iodide salt and sodium/iodide symporter inhibitor, such as perchlorate, may be administered to the intestine of a human or an animal in the form of a capsule, wherein the capsule shell is comprised by gelatin or pullulan or a vegetable capsule.

The activated carbon comprising adsorbed iodine ($I_2$) and/or an adsorbed iodide salt and a sodium/iodide symporter inhibitor may be administered in the same formulated tablet(s) or capsule(s) or in separate tablets or capsules. In one example, the activated carbon comprising adsorbed iodine and/or an adsorbed iodide salt and sodium/iodide symporter inhibitor are administered to the intestine of a human or an animal, in the same tablet(s) or capsule(s), following the daily dosing regimes as previously described. In another example, the activated carbon comprising adsorbed iodine and/or an adsorbed iodide salt and sodium/iodide symporter inhibitor are administered to the intestine of a human or an animal, in different tablets or capsules, following the daily dosing regimes as previously described, with the advantage of better control of any undesired interactions or effects between the sodium/iodide symporter inhibitor and activated carbon comprising adsorbed iodine and/or an adsorbed iodide salt in the stomach or intestine. Furthermore, the activated carbon powder comprising adsorbed iodine and/or an adsorbed iodide salt can be poured in a glass of water and drunk, while the sodium/iodide symporter inhibitor can either be placed in the water or a capsule or tablet.

The activated carbon comprising adsorbed iodine and/or an adsorbed iodide salt and a sodium/iodide symporter inhibitor can be supplied as a kit for obtaining an improved lung function in a human or an animal lung affected by airway obstruction, comprising a first pharmaceutical composition, comprising a pharmacologically effective amount of activated carbon comprising adsorbed iodine and/or an adsorbed iodide salt; and a second pharmaceutical composition, comprising a sodium/iodide symporter inhibitor.

EXAMPLES

Example 1: Preparation of Activated Carbon Samples Loaded Alkali Metal Iodide or Earth Alkali Metal Iodide Materials:
Activated carbon (Sigma C7606), Potassium iodide (Sigma P7744), deionized water. Equipment:
Magnetic stirrer IKA RTC basic, oil bath, reflux condenser, balance XP-300 (Denver instruments), Pyrex glass flask (2 L), polymer-enclosed magnetic bar, vacuum filter flask (2 L), OOH filter paper (Whatman), laboratory drying oven TS80000, Termaks.

Method:
8.0 g KI was dissolved in 1 L of water in an adsorption experiment. Activated carbon (92 g) was added. The suspension was stirred for 12 hours at room temperature (21-23° C.). The activated carbon product was separated from the KI solution by filtration under reduced pressure and dried for 12 h in 75° C. This resulted in a sample consisting of activated carbon impregnated with ~1.6% (wt.) KI. Activated carbon preparations coated with other specific amounts of KI were obtained by repeating example 1 using other amounts of activated carbon and KI. Determination of the amount of adsorbed KI on activated carbon was carried out by three methods, namely conductometry, gravimetric analysis and elemental analysis.

Example 2: Preparation of Iodinated Activated Carbon

Materials: Activated carbon from Sigma C7606; meets USP testing specification. Elemental Iodine from Sigma-Aldrich 03002; meets USP testing. Undenatured ethanol from Kemetyl; meets USP and EP testing specifications with <0.5% water content.

Equipment:

Mixing cylinder 500 ml, measuring cylinder 500 ml, E-flask 50 ml, Büchner funnel Duran diameter 105 ml and stirrer motor with blade, RZR 1 from Heidolph. Filterpaper grade 00H from Munktell. Evaporation dish made from borosilicate glass.

Method: Depending on the batch size, the amount of activated carbon, elemental iodine and ethanol is calculated. For a batch size of 50 g iodinated carbon, 4.5 g of iodine, 45.5 g of activated carbon and 450 ml ethanol is used. The activated carbon is suspended in the measuring cylinder with 410 ml ethanol and the elemental iodine is solved in the E-flask with 40 ml ethanol. The iodine is added, stirred for 2 min and allowed to impregnate the carbon for 1 h. Thereafter, the iodinated activated carbon is separated from the ethanol solution by filtration under reduced pressure and dried for 5 hours at 150° C. This results in iodinated activated carbon impregnated with 9% (wt.) $I_2$. The amount of adsorbed iodine is determined by elemental analysis.

Example 3: Clinical Effect by IAC on Patients with Moderate COPD

The effect of 8 weeks treatment with oral iodinated activated charcoal (IAC) on lung function of patients with moderate chronic obstructive pulmonary disease (COPD) was examined in a double blind randomized placebo controlled parallel group study with 40 patients. In the IAC group, patients showed a statistically significant improvement of $FEV_1$ baseline by 130 ml compared to placebo, corresponding to 8.2% improvement (p=0.031*). Correlation statistics revealed that the improvement of $FEV_1$ baseline was significantly correlated both to $FEV_1$ post-bronchodilator (p=0.0020**) and $FEV_1$ post-exercise (0.0328*) values, which demonstrates that the positive effect by Iodo-Carb is present also on top of a bronchodilator and that patients do not reach a limit for maximal improvement of the lung function. In summary, this study demonstrates that iodinated activated charcoal surprisingly and significantly improved lung function of patients with moderate COPD.

Example 4: Effect by a Combination of Activated Carbon Comprising Adsorbed Iodine and an Inhibitor of the Sodium/Iodide Symporter on Lung Function An 80-year old Caucasian man with moderately severe COPD examined the synergistic effect by a combination of IAC and potassium perchlorate. After having stable lung function for around a month, he took 2.73 g activated charcoal in water daily for 2 weeks. This did not improve his lung function ($FEV_1$). After that, he instead took 270 mg $I_2$ daily in a vegetable capsule daily for 2 weeks. This did not improve his lung function. Thereafter, he instead took 100 mg potassium perchlorate daily for 2 weeks. This did not improve the lung function at all. Following this, he instead took 3 g IAC (prepared according to example 2, and consisting of 2.73 g activated charcoal with 270 mg iodine) daily for 2 weeks. This improved his lung function ($FEV_1$) by 150 ml. Finally, he took a combination of 100 mg potassium perchlorate and 3 g IAC daily for 2 weeks. This improved his $FEV_1$ by 270 ml. Thus, a combination of IAC and perchlorate almost doubled the improvement of his lung function compared to only IAC. This is highly surprising, since potassium perchlorate as a single treatment caused no improvement of the lung function at all. In addition, his cough and sputum production was considerably reduced compared to when he only took IAC or only iodine, only activated charcoal, or only perchlorate.

The invention claimed is:

1. A pharmaceutical composition for obtaining an improved lung function in a human or an animal lung affected by chronic obstructive pulmonary disease (COPD) or asthma, comprising:
   a pharmacologically effective amount of activated carbon comprising adsorbed iodine (I2) and perchlorate; wherein the amount of activated carbon comprising adsorbed iodine and perchlorate is from 1 g to 25 g; wherein the amount of perchlorate is in the range from 50 mg to 250 mg.

2. The pharmaceutical composition according to claim 1, wherein the perchlorate is in the form of a perchlorate salt.

3. The pharmaceutical composition according to claim 1, wherein the pharmaceutical composition is a pharmaceutical composition for oral administration.

4. A method for obtaining an improved lung function in a human or an animal lung affected by chronic pulmonary disease (COPD) or asthma, comprising the step of: administering to the human or animal the pharmaceutical composition of claim 1.

* * * * *